United States Patent [19]

Siclari et al.

[11] Patent Number: 4,791,228

[45] Date of Patent: Dec. 13, 1988

[54] PROCESS FOR PREPARING α,ω-DICARBOXYLIC ACIDS

[75] Inventors: Francesco Siclari, Barlassina; Pier P. Rossi, Garlasco; Luigi Canavesi, Solbiate Olona, all of Italy

[73] Assignee: SNIA Viscosa Societa' Nazionale Industria Applicazioni Viscosa S.p.A., Milan, Italy

[21] Appl. No.: 700,334

[22] Filed: Feb. 12, 1985

Related U.S. Application Data

[63] Continuation of Ser. No. 348,320, Feb. 12, 1982, abandoned, which is a continuation of Ser. No. 90,987, Nov. 5, 1979, abandoned.

[30] Foreign Application Priority Data

Nov. 10, 1978 [IT] Italy ............................. 29682 A/78

[51] Int. Cl.$^4$ .................... C07C 51/235; C07C 51/16
[52] U.S. Cl. .................................. 562/531; 562/524
[58] Field of Search ............................... 562/524, 531

[56] References Cited

U.S. PATENT DOCUMENTS 2,777,865  1/1957  Logan ................................. 562/593
3,043,872  7/1962  Roberts et al. ..................... 562/593
3,714,244  1/1973  Okada et al. ....................... 562/593
3,804,895  4/1974  Schwab .............................. 562/524

FOREIGN PATENT DOCUMENTS 568088  12/1958  Canada .............................. 562/531
2649510  5/1977  Fed. Rep. of Germany ...... 562/531

Primary Examiner—Werren B. Lone
Attorney, Agent, or Firm—Bryan, Cave, McPheeters & McRoberts

[57] ABSTRACT

A process for preparing α,ω-dicarboxylic acids of the formula HOOC—$(CH_2)_n$—COOH in which n=6 to 10 is disclosed. The process consists of the catalytic oxidation of a compound of formula X—$(CH_2)_n$—CHO wherein X is CHO or COOH and n is 6 to 10 by $O_2$ pure or in mixture with inert gas, possibly under pressure, in at least one polar solvent, at a temperature comprised between 20° and 90° C. and in the presence of a catalyst. The catalyst is chosen from the group consisting of at least one cobalt (II) salt and one ferrous salt. The amount of the catalyst is ≦0.001 mol % calculated on the equivalents of the aldehyde groups in the starting compound.

9 Claims, No Drawings

PROCESS FOR PREPARING α,ω-DICARBOXYLIC ACIDS

This is a continuation of application Ser. No. 348,320, filed Feb. 12, 1982, now abandoned, which is a continuation of application Ser. No. 090,987, filed Nov. 5, 1979 (now adandoned).

BACKGROUND OF THE INVENTION

This invention generally relates to a process for preparing α,ω-dicarboxylic acids.

More particularly, this invention provides a process for preparing saturated linear aliphatic α,ω-dicarboxylic acids containing 8 to 12 carbon atoms, by catalytic oxidation of the corresponding aldehyde acids or of the corresponding dialdehydes.

The industrial importance of saturated dicarboxylic acids is known. For example, to state only their main uses, dicarboxylic acids can be used as the primary components or as additives in the manufacture of various types of nylon, fibres and lubricants, and as additives for mineral oils etc.

When dicarboxylic acids are condensed with diamines, the resultant products can also be used as wetting agents and emulsifiers, in particular in the petroleum industry.

It is known to prepare saturated long-chain aliphatic α,ω-dicarboxylic acids by treating the ozonides of cycloolefines with oxidising agents. For example, in U.S. Pat. No. 3,328,250, cyclohexene ozonide is oxidised to adipic acid by ozone.

However, this process is difficult to carry out industrially, as it presents obvious dangers when working with large quantities of material, because it is necessary to evaporate the ozonide solution from the solvent before its oxidative decomposition to formic acid.

It is also known from U.S. Pat. No. 3,383,398 to prepare dicarboxylic acids in a single stage by ozonising cycloolefines in pyridine.

However, this process also finds no easy industrial application because of the high cost of the solvent (pyridine).

R. H. Perry J. and B. G. Coreman (A.C.S.—Div. Petrol Chem. Preprints 12 (2) D-5 to D-10 (1967)) indicate a method for preparing unsaturated long-chain aliphatic α,ω-dicarboxylic acids by the mono-ozonisation of polyunsaturated cycloolefines, followed by oxidation of the formed mono-ozonides in the presence of a heavy metal. This method is especially inconvenient industrially because of the difficulties, not easily overcome, which are encountered in separating the ozonide from the unreacted cycloolefines, in that the conversion of the polyunsaturated cycloolefine into mono-ozonide is very low, and thus at the end of the reaction there is a mixture the greater part of which is cycloolefine and the smaller part ozonide.

Methods are also known (GB No. 767,416, U.S. Pat. No. 3,804,895 and DOS No. 2,649,510) for preparing dicarboxylic acids by oxidising the corresponding aldehyde acids in the presence of oxidation catalysts in a quantity of at least 0.002% of the aldehyde acid by weight. However, with such processes the yields do not exceed 87.5% of the theoretical.

SUMMARY OF THE INVENTION

The Applicant has now surprisingly found that linear aliphatic α,ω-dicarboxylic acids containing 8 to 12 carbon atoms can be prepared by oxidising the corresponding aldehyde acids or dialdehydes, with exceptional yields and conversions if the oxidation is carried out in the presence of at least one cobalt (II) and/or ferrous compound in a quantity which is $\leq 0.001$ mol % of the equivalents of the —CHO groups in the starting compound.

The present invention therefore provides a process for preparing α,ω-dicarboxylic acids of formula

HOOC—(CH$_2$)$_n$—COOH in which n=6 to 10, by the catalytic oxidation of a compound of formula (1)

X—(CH$_2$)$_n$—CHO        (1)

in which X=CHO or COOH, and n has the meaning heretofore indicated, by molecular oxygen either in its pure state or in mixture with inert gas and possibly under pressure, in an evironment of at least one polar solvent at a temperature between 20° and 90° C. and in the presence of a catalyst chosen from the group consisting of at least one cobalt (II) salt and one ferrous salt, wherein said catalyst is present, with respect to the aldehyde acid or dialdehyde, in a quantity $\leq 0.001$ mol % calculated on the equivalents of the aldehyde groups in the starting compound.

DESCRIPTION OF THE PREFERRED EMBODIMENT OF THE INVENTION

By means of the process according to the invention, i.e. by oxidising the compound of formula (1) in the presence of the aforesaid quantity of catalyst, the corresponding dicarboxylic acids are obtained with a yield $\geq 90\%$, and in particular cases 97% or more.

The compounds of formula (1) used as the starting material in the process according to the invention are either known compounds or can be prepared by known conventional methods.

The catalytic oxidation of the compound of formula (1) is advantageously carried out in a neutral, alkaline or preferably acid solution, possibly in aqueous mixture. In the preferred case in which an acid solvent is used, this can be monocarboxylic acid, such as acetic acid.

The catalytic oxidation is carried out according to the invention preferably at a temperature between 40° and 60° C.

The preferred oxidation catalyst is for example cobalt (II) acetate tetrahydrate, iron (III) acetate or their mixtures.

The α,ω-dicarboxylic acid so obtained is isolated and purified by known conventional methods.

The present invention also relates to the α,ω-dicarboxylic acids prepared by the process according to the invention.

The examples given hereinafter illustrate the present invention, but without limiting it.

EXAMPLES 1 TO 16

Oxidation of Saturated Dialdehyde in the Presence of Co (II)

The oxidation is carried out directly on a saturated dialdehyde or a saturated aldehyde acid of high purity.

200 g of decamethylenedialdehyde or 200 g of formylundecanoic acid dissolved in 1800 cc of 85% acetic acid are placed in a glass autoclave. The temperature is raised to 60° C., a quantity of catalyst is added (cobalt (II) acetate tetrahydrate, ferrous acetate or a mixture thereof) varying from 0.001 to 0.000125% (calculated as cation with respect to the equivalents of the aldehyde groups present in the starting compound).

It is subjected to magnetic stirring, and oxygen is absorbed at a pressure varying from atmospheric pressure to 10 atm, measurements being made by an absorption gas meter. The $O_2$ absorption varies from 90 to 103% of the theoretical.

The dodecanedioic acid thus prepared is allowed to crystallise by cooling the solution, which is then filtered. The filtrate is evaporated to dryness.

The yield indicated in the table represents the oxidation yield measured by gas chromatograph analysis on the precipitate and residue.

Examples 13 to 16 are comparison examples, in which a quantity of catalyst exceeding 0.001 mol % is used, calculated on the equivalents of the aldehyde groups present in the starting compound $\alpha$ or $\beta$.

temperature from 20° to 90° and in the presence of an effective amount of catalyst selected from the group consisting of cobalt (II) salts, ferrous salts and mixtures thereof, said catalyst being present in a quantity with respect to the aldehyde acid or dialdehyde, of about 0.0005 mole %, calculated as the cation, on the equivalents of the aldehyde groups on the staring compound of formula (1).

2. The process of claim 1, wherein the compound of formula (1) is selected from the group consisting of decamethylenedialdehyde and formylundecanoic acid, the catalyst is cobalt (II) acetate tetrahydrate, or ferrous acetate and the reaction temperature is between 40° and 60°.

3. A process as claimed in claim 1, wherein the catalyst used is cobalt (II) acetate tetrahydrate.

4. A process as claimed in claim 1, wherein the catalyst used is iron (II) acetate.

5. A process as claimed in claim 1, wherein the cata-

TABLE

| Example | Starting compound | Catalyst | Mol % of catalyst* | Mol % of $O_2$ absorbed | Dodecanedioic acid yield % | Melting point of product °C. |
|---|---|---|---|---|---|---|
| 1 | $\alpha$ | A | 0.0005 | 101 | 97 | 121–124 |
| 2 | $\alpha$ | A | 0.0005 | 100 | 92 | 117–121 |
| 3 | $\alpha$ | A | 0.00025 | 100 | 93 | 119–121 |
| 4 | $\alpha$ | A | 0.000125 | 91 | 94.5 | 123–124 |
| 5 | $\alpha$ | C | 0.0005 | 101 | 94 | 121–123 |
| 6 | $\alpha$ | C | 0.00025 | 102 | 97 | 121–124 |
| 7 | $\alpha$ | C | 0.001 | 99 | 97.5 | 121–125 |
| 8 | $\alpha$ | C | 0.001 | 103 | 95.5 | 114–120 |
| 9 | $\alpha$ | B | 0.0005 | 102 | 90.5 | 120–122 |
| 10 | $\beta$ | A | 0.001 | 90 | 94 | 118–122 |
| 11 | $\beta$ | A | 0.0005 | 95 | 97.5 | 121–123 |
| 12 | $\beta$ | A | 0.00025 | 98 | 98 | 120–123 |
| 13 | $\beta$ | A | 0.005 | 80 | 83 | 110–115 |
| 14 | $\alpha$ | A | 0.005 | 83.5 | 82 | 111–114 |
| 15 | $\alpha$ | A | 0.01 | 115 | 82 | 110–118 |
| 16 | $\alpha$ | B | 0.005 | 90 | 78 | 117–121 |

Table legend:
A = cobalt (II) acetate tetrahydrate
B = ferrous acetate
C = 50% by weight of A + 50% by weight of B
$\alpha$ = decamethylenedialdehyde
$\beta$ = formylundecanoic acid
* = molar percentage calculated on the equivalents of the aldehyde groups present in the starting compound ($\alpha$ or $\beta$).

What is claimed is:

1. A process for preparing $\alpha,\omega$-dicarboxylic acids of the formula $$HOOC-(CH_2)_n-COOH$$

in which n is 6 to 10, comprising reacting a compound of the formula $$X-(CH_2)_n-CHO \qquad (1)$$

in which X is CHO or COOH, and n is 6 to 10, with molecular oxygen in the presence of acetic acid at a lyst used is a mixture of cobalt (II) acetate tetrahydrate and iron (II) acetate.

6. A process as claimed in claim 1, wherein the compound of formula (1) is 11-formylundecanoic acid.

7. A process as claimed in claim 1, wherein the compound of formula (1) used is decamethylenedialdehyde.

8. A process as claimed in claim 1, wherein the reaction is carried out at a temperature of between 40° and 60° C.

9. The process of claim 1, wherein the pressure is between 1 and 10 atm.

* * * * *